United States Patent
Kröner et al.

(10) Patent No.: US 7,292,673 B2
(45) Date of Patent: Nov. 6, 2007

(54) DUAL MODALITY TOMOGRAPHY APPARATUS WITH A PATIENT SUPPORT DEVICE

(75) Inventors: Hans-Jürgen Kröner, Baiersdorf (DE); Michael Loser, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/250,337

(22) Filed: Oct. 13, 2005

(65) Prior Publication Data
US 2006/0109959 A1    May 25, 2006

(30) Foreign Application Priority Data
Oct. 13, 2004   (DE) .................. 10 2004 049 915

(51) Int. Cl.
*G21K 1/12*   (2006.01)
*G21K 23/04*  (2006.01)
*A61B 6/04*   (2006.01)
*G01T 1/164*  (2006.01)

(52) U.S. Cl. .................. 378/20; 378/63; 378/209; 250/363.03

(58) Field of Classification Search ............ 378/4, 378/208, 209, 20, 195, 63, 68; 5/600, 601; 250/363.03, 363.04
See application file for complete search history.

(56) References Cited

U.S. PATENT DOCUMENTS

| | | | |
|---|---|---|---|
| 5,013,018 A | 5/1991 | Sleek et al. | |
| 6,473,918 B2 | 11/2002 | Schaefer | |
| 6,490,476 B1 | 12/2002 | Townsend et al. | |
| 6,631,284 B2* | 10/2003 | Nutt et al. | 600/427 |
| 6,895,105 B2* | 5/2005 | Wollenweber | 382/131 |
| 2002/0180397 A1 | 12/2002 | Henley et al. | |
| 2003/0058984 A1* | 3/2003 | Susami et al. | 378/19 |
| 2005/0082487 A1* | 4/2005 | Amano | 250/363.03 |
| 2005/0207530 A1* | 9/2005 | Inoue et al. | 378/63 |

* cited by examiner

*Primary Examiner*—Edward J. Glick
*Assistant Examiner*—Irakli Kiknadze
(74) *Attorney, Agent, or Firm*—Schiff Hardin LLP

(57) ABSTRACT

A tomography apparatus that has a support device that can be displaced in a displacement direction for supporting a subject, and at least two acquisition systems disposed in succession in the displacement direction of the support device. The support device has a base that can be displaced relative to the floor and a support plate that can be displaced in the displacement direction relative to the base, such that data acquisitions at respective acquisition positions in the respective acquisition systems under essentially identical acquisition conditions are possible in a simple manner.

7 Claims, 2 Drawing Sheets

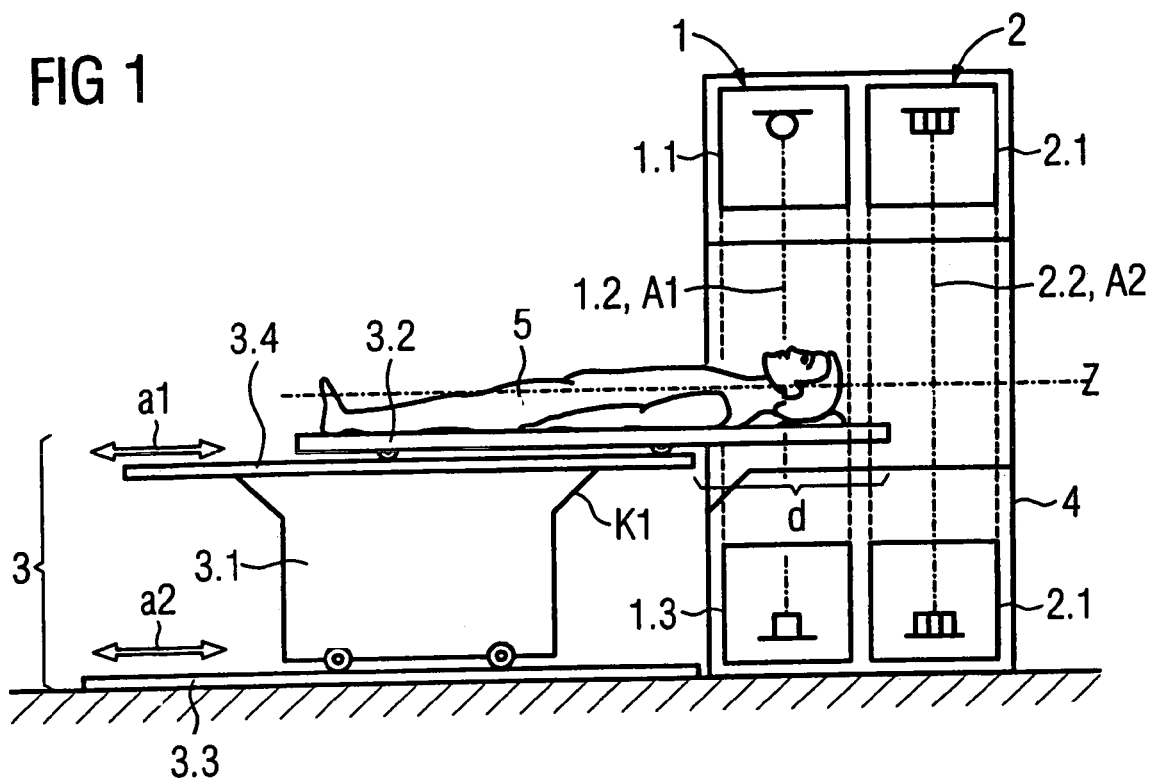
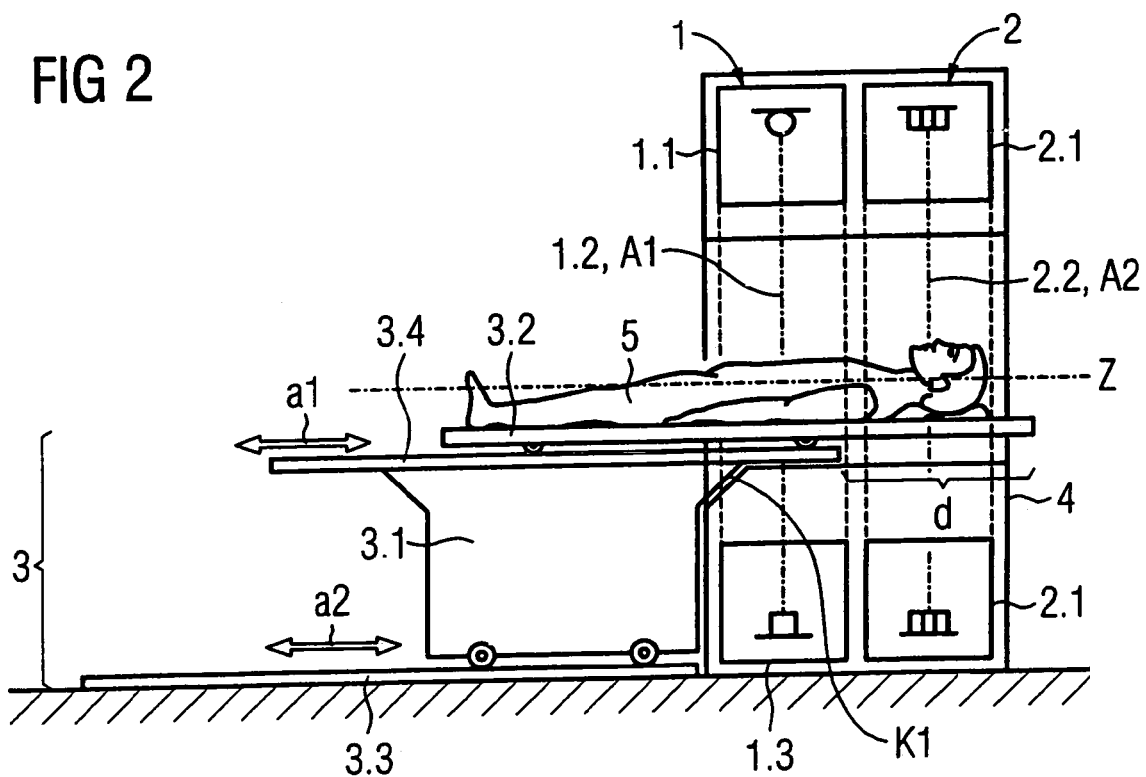

DUAL MODALITY TOMOGRAPHY APPARATUS WITH A PATIENT SUPPORT DEVICE

BACKGROUND OF THE INVENTION

1. Field of the Invention

The present invention concerns a tomography apparatus of the type having a support device (that can be moved in a displacement direction) for supporting a subject and with two acquisition systems disposed in succession in the displacement direction of the support device.

2. Description of the Prior Art

A dual modality tomography apparatus with a support device for a patient and with two acquisition systems (namely a computer tomography (CT) acquisition system and a positron emission tomography (PET) acquisition system) disposed one after the other in the displacement direction is known from U.S. Pat. No. 6,490,476. The support device has a support plate that can be moved relative to the base so that the patient can be shifted between the two acquisition systems. The image data acquired with the respective acquisition systems contain various types of image information and are geometrically fused with one another for a later diagnosis. A simple geometric fusion of the images is, however, only possible when the examination region containing diagnostically relevant information has been acquired by both acquisition systems under the same acquisition conditions, in particular with the same geometric alignment of the subject relative to the acquisition system.

So that the subject is not displaced from the position perpendicular to the acquisition systems upon shifting of the support plate between the acquisition systems, in such a tomography apparatus a support plate is used that exhibits a high rigidity. Achieving such a stiffness of the support plate is possible only with a high cost.

SUMMARY OF THE INVENTION

An object of the present invention is to provided a tomography apparatus that allows data acquisitions with at least two acquisition systems arranged one after the other to be accomplished in a simple manner at the respective acquisition positions under essentially the same acquisition conditions.

This object is achieved by a tomography apparatus according to the invention having a support device, adjustable in a displacement direction, for supporting a subject and at least two acquisition systems disposed in succession in the displacement direction, wherein the support device has a base that can be adjusted (moved) relative to the floor and a support plate that can be adjusted (moved), in the displacement direction relative to the base.

Due to the additional adjustment capability of the base relative to the floor, the subject to be examined in the inventive tomography apparatus can be positioned relative to the respective acquisition system so that the same adjustments of the support plate with regard to the base are possible so that the patient can be moved to the same acquisition position in each acquisition system. In this manner it is ensured that the data acquisitions ensue under essentially the same acquisition conditions in both acquisition systems, even given deflection of the support plate.

The inventive tomography apparatus thus enables the use of a standard support plate which is elastically-deformable to a certain degree, such that a cost-intensive stiffening can be foregone.

In an embodiment of the invention, the base can be displaced so that the subject can be brought into a first acquisition position relative to the first acquisition system and can be brought into a second acquisition position relative to the second acquisition system, such that data from the same scan region can be acquired with each acquisition system.

So that the support plate is deflected the same degree at each acquisition position in each acquisition system so as to ensure the same acquisition conditions, in the set first acquisition position and in the set second acquisition position the support plate exhibits the same orientation relative to the base.

Starting from the first or the second acquisition position, data from the scan region can be acquired solely by displacement of the support plate. Given displacement of the support plate, the base remains in an unchanged position relative to the floor so that the same deflection of the support plate within the entire scan region also exist at each acquisition position in each acquisition system. Thus, a simple geometric fusion of the respective images acquired from the acquisition systems is possible for the entire scan region.

The first acquisition system preferably is an x-ray computed tomography (CT acquisition system and the second acquisition system preferably is a positron emission (PET) acquisition system. The images that can be generated by the CT acquisition system essentially contain anatomical information of an examined subject region, while the images that can be generated by the PET acquisition system primarily contain physiological information. By the use of such acquisition systems, a physician can make a more precise diagnosis on the basis of a geometrically-fused image which contains both anatomical and physiological information.

So that data from the subject can be acquired as completely as possible by both acquisition systems in the displacement direction, for unhindered movement of the support device the base has a contour adapted to the housing of the tomography apparatus.

Rails are preferably provided for simple displacement of the base relative to the floor. A support device with a base that can be displaced on rails is known from U.S. Pat. No. 5,013,018 and from DE 60004014 T2.

DESCRIPTION OF THE DRAWINGS

FIG. 1 shows an inventive tomography apparatus in a side view with a support device in a first acquisition position relative to a first acquisition system.

FIG. 2 shows the tomography apparatus of FIG. 1, with the support device in a second acquisition position relative to a second acquisition system.

DESCRIPTION OF THE PREFERRED EMBODIMENTS

Figure 3:
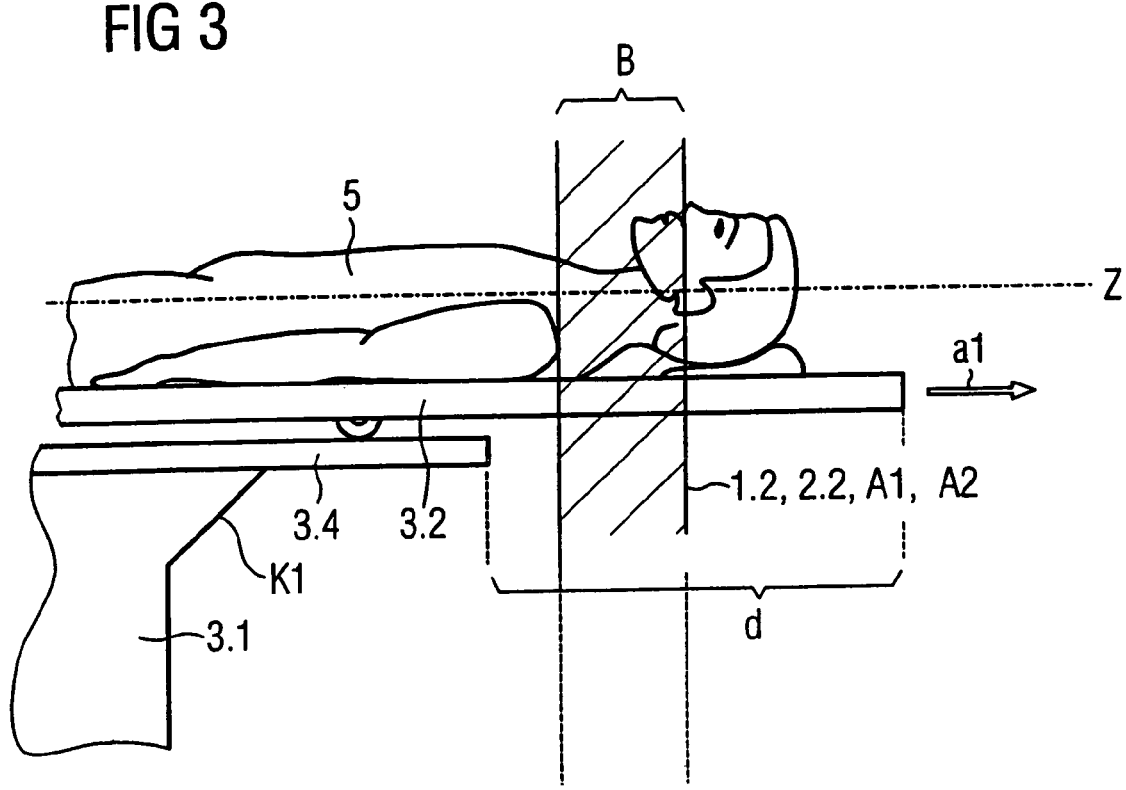
FIG. 3 shows a section of the support device of FIG. 1 or FIG. 2 in either the first or second acquisition position, with a marked scan region.

In a side view, FIG. 1 shows an inventive tomography apparatus with two acquisition systems 1, 2 arranged one after the other in the displacement directions a1, a2, and a support device 3 (which can be displaced in the displacement directions a1, a2) in a first acquisition position A1 relative to the first acquisition system 1. In the shown example the first acquisition system is a CT acquisition system 1 and the second acquisition system is a PET acquisition system 2. The support device has a base 3.1 that can be displaced on rails 3.3 relative to the floor and a support plate 3.2 (that can be displaced relative to the base 3.1 and likewise supported on rails 3.4 in this example) for supporting a subject, in this case a patient 5.

The CT acquisition system 1 has an x-ray radiator 1.1 and a CT detector 1.3 mounted opposite one another on a rotary frame (not shown) such that, in operation of the CT acquisition system 1, an x-ray beam emanating from a focus of the x-ray radiator 1.1 strikes on the CT detector 1.3. The rotary frame can be offset in rotation around a system axis Z by an actuation device (not shown). The raw data acquired by the CT detector 1.3 from different projection directions relative to a CT acquisition plane 1.2 enable reconstruction of CT images in the form of slice or volume images and essentially serve for visualization of anatomical information of the inside of a body of the patient 5.

The PET acquisition system 2 arranged following the CT acquisition system 1 has an annular PET detector 2.1 for detection of gamma quanta generated by scattering upon decay of a positron. The raw data acquired by the PET detector 2.1 with regard to a PET acquisition plane 2.2 enable reconstruction of a PET image that, in contrast to the CT image, significantly visualizes physiological information of the inside of a body of the patient 5.

The two acquisition systems 1, 2 do not necessarily have to be a CT acquisition system and a PET acquisition system. Other acquisition systems such as, for example, ultrasound acquisition systems can be used. Moreover, the inventive tomography apparatus is also not limited to specific number of acquisition systems. For example, a third acquisition system arranged after the first and the second acquisition systems in the displacement direction can additionally be provided.

The support device in FIG. 1 is located in a first acquisition position A1 relative to the CT acquisition system 1. In the shown example, the support plate 3.2 exhibits a projection d at the first acquisition position A1 relative to the base 3.1, such that the support plate 3.2 bends (in a manner not indicated) due to the body weight of the patient 5 present in the region of the projection d. Due to the curvature (deflection) of the support plate 3.2, the patient 5 is also displaced from the original position in a direction perpendicular to the displacement direction during data acquisition with the CT acquisition system 1.

Figure 4:
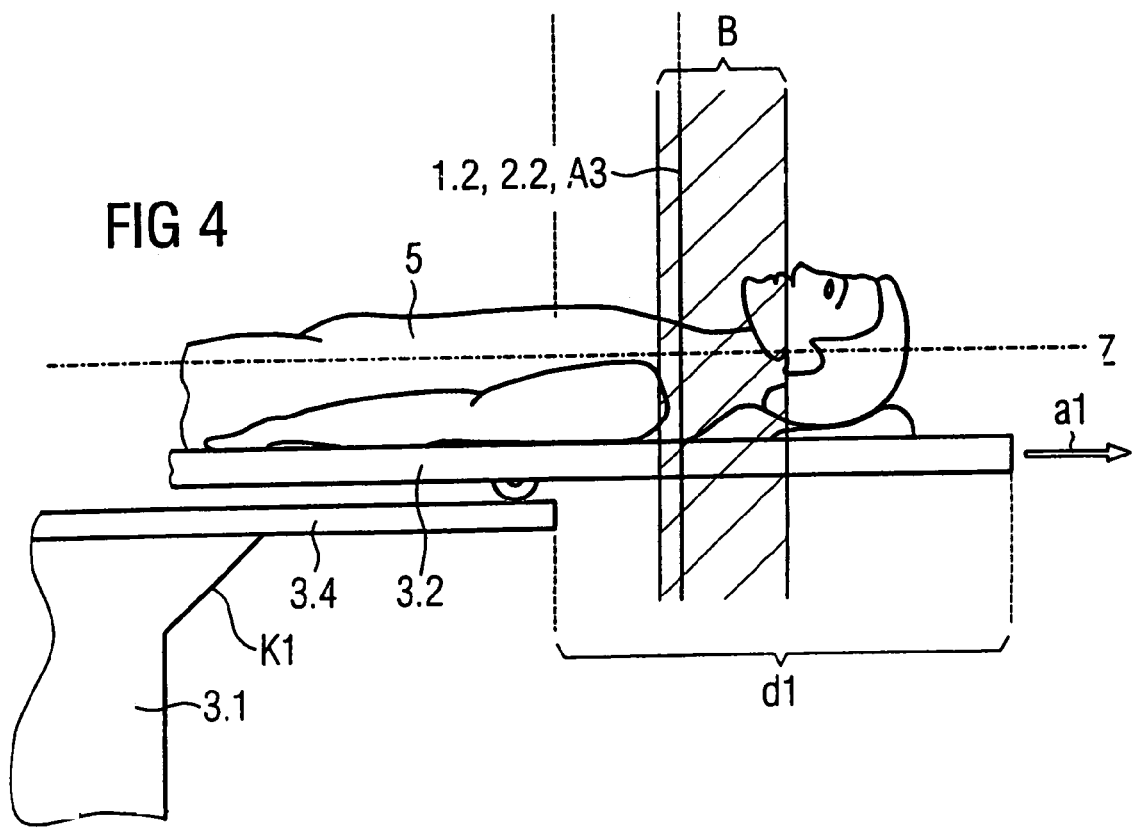
FIG. 4 shows the support device of FIG. 3 in a scan position within the scan region.

Starting from this first acquisition position A1, a first entire scan region B shown in FIG. 3 and FIG. 4 can be acquired with the CT acquisition system by displacement of the support device 3. For scanning the scan region B, the support device 3 is merely displaced by shifting the support plate 3.2. The base 3.1 remains at an unchanged position during the scanning of the scan region B.

After acquisition of the scan region B with the CT acquisition system 1, the support device 3 is shifted into a second acquisition position A2 (shown in FIG. 2) relative to the PET acquisition system 2. A shifting of the support device 3 from the first acquisition position A1 into the shown second acquisition position A2 preferably ensues solely by displacement of the base 3.1. For unhindered movement of the support device 3 with regard to the two acquisition systems, the base 3.2 exhibits a contour K1 adapted to the housing of the tomography apparatus 4.

Images from the CT acquisition system 1 and from the PET acquisition system 2 that are acquired under the same acquisition conditions, i.e. with the same curvature of the support plate 3.2, can easily be geometrically fused with one another without elaborate correction. In the second acquisition position A2, the support plate 3.2 therefore exhibits the same projection d in comparison with the first acquisition position A1, such that the curvatures of the support plate 3.2 are identical in the first acquisition position A1 and the second acquisition position A2. The acquisition with the PET acquisition system 2 occurs under an acquisition condition essentially identical to that of the CT acquisition system 1, such that the images of both acquisition systems can easily be geometrically fused.

As is also the case in the scanning if the scan region B starting from the first acquisition position A1, the scanning of the scan region B starting from the second acquisition position A2 ensues by a movement of the support plate 3.2 so that the support plate 3.2 exhibits the same projection relative to the base 3.1 in each of the acquisition positions A1, A2 of each of the acquisition systems 1, 2. It is thereby ensured that corresponding images of both acquisition systems 1, 2 can be acquired with the same curvature of the support plate 3.2 within the entire subject region B, such that a simple fusion of the images for the entire scan region is possible due to the respective, same acquisition conditions. This fusion takes place in an image-fusing computer 6.

FIG. 3 shows a section of the support device 3 with the patient 5 from FIG. 1 or FIG. 2 in the first or the second acquisition position A1 or A2, wherein a scan region B to be examined is marked abutting the respective acquisition position A1 or A2. The scanning of the scan region B ensues starting from the respective acquisition position A1 or A2 by a continuous movement of the support plate 3.2 in the marked displacement direction, with the base 3.1 remaining in an unchanged position.

A scan position A3 within the scan region B relative to the respective acquisition systems 1, 2 during the movement of the support plate 3.2 is exemplarily shown in FIG. 4. The projection d1 (changing due to the continuous movement of the support plate 3.2) has the effect that the curvature of the support plate 3.2 also continuously varies, such that different acquisition conditions result at different scan positions within the scan region B. However, it is important only that the same acquisition conditions be present for corresponding scan positions between the two acquisition systems 1, 2 so that a correct geometric fusion of the images acquired from the acquisition systems is possible.

As already explained, this is ensured by the base 3.1 remaining unchanged relative to the floor during the scanning of the acquisition region B, such that the scanning of the scan region B is effected solely by a movement of the support plate 3.2, so the setting of the support plate 3.2 relative to the base 3.1 is identical given corresponding scan positions between the two acquisition systems 1, 2.

Although modifications and changes may be suggested by those skilled in the art, it is the intention of the inventors to embody within the patent warranted hereon all changes and modifications as reasonably and properly come within the scope of their contribution to the art.

We claim as our invention:
1. A dual modality tomography apparatus comprising:
   a patient support device having a base adapted for mounting on a floor, said base being displaceable relative to the floor, and having a support plate adapted to receive a patient thereon, said support plate being displaceable along a displacement direction relative to said base, said support plate being deflected by a deflection curvature of the plate toward the floor due to the weight of the patient thereon;

a first data acquisition system for a first tomography modality, and a second data acquisition system for a second tomography modality, said first and second data acquisition systems being disposed in succession along said displacement direction, said support plate being displaceable within each of said first and second data acquisition systems without changing said deflection curvature of the plate to allow each of said first and second data acquisition systems to acquire a set of image data from a same scan region of the patient on said support plate, with said plate exhibiting the same position in each of the sets of image data respectively acquired by the first and second data acquisition system; and a computer that geometrically fuses said sets of data respectively acquired by said first and second data acquisition systems into a single image of said scan region with no compensation for said deflection curvature.

2. A tomography apparatus as claimed in claim 1 wherein said base is displaceable relative to the floor to allow the patient to be moved to a first data acquisition position relative to the first data acquisition system, and to a second data acquisition position relative to the second data acquisition system, allowing data to be acquired from said same scan region of the patient with each of said first data acquisition system and said second data acquisition system.

3. A tomography apparatus as claimed in claim 2 wherein said support plate has a same orientation relative to said base in each of said first data acquisition position and said second data acquisition position.

4. A tomography apparatus as claimed in claim 2 wherein said first data acquisition system and said second data acquisition system each acquire data from said scan region solely by displacement of said support plate.

5. A tomography apparatus as claimed in claim 1 wherein said first tomography modality is an x-ray computed tomography apparatus and wherein said first data acquisition system is an x-ray computed tomography data acquisition system, and wherein said second imaging modality is PET system and wherein said second data acquisition system is a positron emission data acquisition system.

6. A tomography apparatus as claimed in claim 1 comprising a housing containing said first and second data acquisition systems, said housing having a housing contour and wherein said base has a base contour conforming to said housing contour allowing unhindered movement of said base and said support plate relative to said housing.

7. A tomography apparatus as claimed in claim 1 comprising rails adapted for mounting on the floor, and engaging said base to allow displacement of said base relative to the floor.

* * * * *